US011399726B2

(12) United States Patent
Campo et al.

(10) Patent No.: US 11,399,726 B2
(45) Date of Patent: Aug. 2, 2022

(54) DEVICE FOR ANALYSING CARDIOVASCULAR PARAMETERS OF AN INDIVIDUAL

(71) Applicant: WITHINGS, Issy les Moulineaux (FR)

(72) Inventors: David Campo, Boulogne Billancourt (FR); Bastien Rechke, Sevres (FR); Xianzhi Zhang, Paris (FR); Mélanie Patel Alsberghe, Paris (FR); Victor Ting, Issy les Moulineaux (FR); Olivier Bienvenu, Palaiseau (FR)

(73) Assignee: WITHINGS, Issy les Moulineaux (FR)

( * ) Notice: Subject to any disclaimer, the term of this patent is extended or adjusted under 35 U.S.C. 154(b) by 336 days.

(21) Appl. No.: 16/494,073

(22) PCT Filed: Mar. 13, 2018

(86) PCT No.: PCT/FI2018/050178
§ 371 (c)(1),
(2) Date: Sep. 13, 2019

(87) PCT Pub. No.: WO2018/167362
PCT Pub. Date: Sep. 20, 2018

(65) Prior Publication Data
US 2020/0121197 A1    Apr. 23, 2020

(30) Foreign Application Priority Data
Mar. 15, 2017    (EP) ..................... 17161112

(51) Int. Cl.
*A61B 5/0225*    (2006.01)
*A61B 5/0235*    (2006.01)
(Continued)

(52) U.S. Cl.
CPC .......... *A61B 5/0225* (2013.01); *A61B 5/0235* (2013.01); *A61B 5/282* (2021.01);
(Continued)

(58) Field of Classification Search
CPC ..... A61B 5/0225; A61B 5/0235; A61B 5/282; A61B 5/6824; A61B 5/6831;
(Continued)

(56) References Cited

U.S. PATENT DOCUMENTS

2001/0012916 A1* 8/2001 Deuter ............... A61B 5/02125
600/485
2004/0158162 A1   8/2004 Narimatsu
(Continued)

FOREIGN PATENT DOCUMENTS

CN        102949186 A     3/2013
EP          2191771 A1    6/2010
WO    WO 2016/161228 A1  10/2016

OTHER PUBLICATIONS

International Search Report and Written Opinion related to Application No. PCT/FI2018/050178 dated Aug. 1, 2018.

*Primary Examiner* — Allen Porter
*Assistant Examiner* — Abid A Mustansir
(74) *Attorney, Agent, or Firm* — von Briesen & Roper, s.c.

(57) ABSTRACT

A device for collecting cardiovascular data relating to an individual user, comprising a control unit assembly with an electronic controller and a pneumatic unit, an arm band having an inflatable bladder and configured to surround the left arm of the individual, wherein the pneumatic unit has a pump and a pressure sensor, and is configured to inflate and deflate the inflatable bladder, so that the electronic controller can determine the arterial pressure of the user, the device further comprising an acoustic sensor being coupled to the external wall of the arm band and having a sensitive side such that in use configuration, the sensitive side is adjacent to the chest of the user, whereby at least a cardiovascular timing characteristic can be inferred from signals from the (Continued)

acoustic sensor and the pressure sensor. The device may also comprise a set of contact electrodes to provide additionally ECG functionality.

17 Claims, 7 Drawing Sheets

(51) Int. Cl.
    *A61B 5/00*     (2006.01)
    *A61B 5/282*     (2021.01)

(52) U.S. Cl.
    CPC .......... *A61B 5/6824* (2013.01); *A61B 5/6831* (2013.01); *A61B 2562/0204* (2013.01)

(58) Field of Classification Search
    CPC . A61B 2562/0204; A61B 7/003; A61B 5/681; A61B 2560/0425; A61B 2560/0443; A61B 5/022; A61B 5/02125; A61B 7/04
    See application file for complete search history.

(56) References Cited

U.S. PATENT DOCUMENTS

| | | | |
|---|---|---|---|
| 2009/0018409 A1 | 1/2009 | Banet et al. | |
| 2011/0028853 A1* | 2/2011 | Sano | A61B 5/02141 |
| | | | 600/490 |
| 2013/0261474 A1* | 10/2013 | Kim, I | A61B 5/022 |
| | | | 600/493 |
| 2015/0164344 A1* | 6/2015 | Jouria | A61B 5/02233 |
| | | | 600/301 |

\* cited by examiner

DEVICE FOR ANALYSING CARDIOVASCULAR PARAMETERS OF AN INDIVIDUAL

CROSS-REFERENCE TO RELATED APPLICATION

This Application is a 35 USC § 371 US National Stage filing of International Application No. PCT/FI2018/050178 filed on Mar. 13, 2018 and claims priority under the Paris Convention to European Patent Application No. 17161112.2 filed on Mar. 15, 2017.

FIELD OF THE DISCLOSURE

The present disclosure relates to devices for analysing cardiovascular parameters of an individual and methods carried out thereof. More particularly, it relates to a device configured to sense arterial pressure of such individual and configured to collect other information about cardiovascular parameters, thanks to analysis of electrical and/or acoustic signals emitted by the heart of such individual.

BACKGROUND OF THE DISCLOSURE

There is known devices that combine arterial pressure sensing means and electrocardiogram sensing means, of the type for example disclosed in document US2012283583.

However, this kind of device requires a specific installation, and requires two units linked together by a hose, which is cumbersome. Therefore, the inventors have identified a need to streamline such devices, to simplify the use of such devices and to enhance functionalities.

SUMMARY OF THE DISCLOSURE

According to one aspect of the present disclosure, it is disclosed a device for collecting cardiovascular data relating to an individual user, comprising:
  a control unit assembly (1) with an electronic controller (6) and a pneumatic unit (5),
    an arm band (2) having an inflatable bladder and an internal wall, and configured to surround the left arm of the individual, with the internal wall in contact with the arm's skin, wherein the pneumatic unit has at least a pump (7) and a pressure sensor (61), and is configured to inflate and deflate the inflatable bladder, and wherein the electronic controller is configured to control the pneumatic unit and to determine at least the arterial pressure of the user,
the device further comprising an acoustic sensor (4) being coupled to the external wall of the arm band and having a sensitive side (41) oriented away from the internal wall of the arm band,
such that in use configuration, the sensitive side is adjacent to the chest of the user, whereby at least a cardiovascular timing characteristic can be inferred from signals from the acoustic sensor and the pressure sensor.
Thereby, the electronic controller acquires acoustic signals, sensed by the acoustic sensor, in timely conjunction with pressure wave signals to determine therefrom for example a pulse Transit Time (PTT) from the aortic valve to the brachial artery. Determination of pulse Transit Time (PTT) can be made through a single device, without recourse to wired sensor applied somewhere on the such as electrodes or the like.

According to one particular option, the device further comprising a set of contact electrodes (3) for electrocardiographic sensing, the set of contact electrodes (3) comprising at least first and second contact electrodes (31, 32) for electrocardiographic sensing, the first electrode (31) being arranged in the internal wall (26) of the arm band, the second electrode being arranged at an external wall of the control unit assembly (1) in a position easily accessible by the hand (MD) of the right arm of the user.

Therefore the first contact electrode benefits from the pressure exerted by the band which optimizes the quality of the contact and thus the quality of the ECG measurement. Likewise, the second electrode can be naturally seized by the right hand of the user, hence giving way to a good contact quality at this place.

Electric signals from these ECG electrodes can be used to determine the so-called QRS complex. The electronic controller can use this QRS waveform in timely conjunction with pressure wave signals to determine, according to an alternative method, a Pulse Arrival Time (PAT) defined as the duration between the ventricular depolarization to the arrival of the pressure pulse at the pressure sensor.

According to one particular option, the control unit assembly (1) forms a convex body that can be easily and naturally seized by fingers of user, namely the thumb and at least one or more of the other fingers. The housing forms a natural shape to be gripped/seized.

According to one particular option, the arm band (2) comprises a first portion (21) which has a structural resilience and a second portion (22) which is formed as a flexible extension of the first portion, and fitted with attaching means.

The second portion allows adaptation to various circumference/diameter of arm to be wrapped (D2); the device is easy to install and to tighten thereafter.

According to one particular option, the first portion (21) houses the inflatable bladder. The integrated hose can be thus very short; even, in one configuration, such a hose is not necessary since a direct connection is provided through a pneumatic connector.

According to one particular option, the attaching means comprise loop and hook pads (28, 29), a loop pad at one location and a hook pad at another location, such that adjustment and securing of various encompassed circumference/diameters (D2) of user's arm is made available and very convenient. Such loop and hook solution provides an unlimited number of attach and release maneuvers with unquantized adjustment possibilities (this means a complete freedom of adjustment).

According to one particular option, the device may further comprise a buckle 9, attached to one end 21a of the first portion. A return portion of the second portion can be inserted into the buckled, folded back and attached thereto; this allows attaching firmly the band before pressurization, without covering the acoustic sensor and without covering the control unit assembly.

According to one particular option, the first and second portions (21, 22) have substantially the same height (H). Thereby, the applied pressure is homogenous all around the arm, whatever the diameter D2 may be. Roll-up is easy to achieve stowing configuration.

According to one particular option, the control unit assembly (1) and the first portion (21) have substantially the same height (H). This provides convenience for handling and compact stowed configuration.

According to one particular option the control unit assembly and the first and second portions (21, 22) have substantially the same height H. This enables to apply pressure homogeneously all around the arm, and furthermore, roll-up is easy to achieve stowing configuration.

According to one particular option, the first portion is formed, at rest position and in use configuration, as a portion of cylinder having a main axis Z. Installation of the device around the arm prior to inflating is facilitated.

According to one particular option, the arm band (2) comprises an elastic armature (25). Such an elastic armature provides a sufficient resilience and self-standing structural basis.

According to one particular option, the cumulative length of the first and second portions namely L1+L2 is such that encompassed arm circumference can be comprised generally between 20 cm and 62 cm. Practical adaptation to very different arm configurations is easy, for example from a child arm to a strong sporty arm or an arm of an person suffering from obesity. In a baseline version, L1+L2 is such that encompassed arm circumference can be comprised generally between 22 cm and 42 cm, which suits a large proportion of the adult population.

According to one particular option, the set of contact electrodes (3) comprises a third contact electrode 33, arranged in the internal wall of the first portion of the arm band. This third contact electrode serves as a reference voltage. This improves quality and electrical immunity of the resulting ECG.

According to one particular option, first and third contact electrodes are coupled to the controller through conductive flexible tracks. Wired connection is established whatever the spatial configuration. Said conductive flexible tracks are thereby integrated between the internal layer and the external layer of the armband.

According to one particular option, the pneumatic unit may further comprise a discharge valve, a check valve, and a pressure sensor. These are suitable means to inflate and deflate the bladder.

According to one particular option, the pneumatic unit may be connected to the bladder by a piping. This provides flexibility in the space configuration between the pneumatic unit and the bladder.

According to one particular option, the pneumatic unit may be connected directly to the bladder by a connector. This facilitates integration and provides a compact solution.

According to one particular option, the acoustic sensor is fixedly attached to the external wall of the arm band. The first portion of the band structurally supports the acoustic sensor. This provides ruggedness and simple design.

According to one particular option, the acoustic sensor is removably attached to the external wall of the arm band. The acoustic sensor can be moved to another area of the chest to complement sound analysis. This also can help supporting a remote diagnostic functionality.

According to one particular option, the acoustic sensor is coupled to the first portion with contact pins. Acoustic sensor can be detached from the armband, an extension cord can be inserted therebetween, and the acoustic sensor can be moved to another area of the chest to complement sound analysis. Acoustic sensor can be placed at the classic auscultation spots.

According to one particular option, the device further comprises a display. This provides a basic feed back to the user. This allows user interaction, including user selection among a plurality of usual users, for example in a family.

According to one particular option, the display is arranged on the control unit assembly (1). This improves mechatronic integration. This provides a simple man machine interface.

According to one particular option, the device forms an integral unit. It proves to be a particularly convenient configuration for use and stow away use cases.

According to one particular option, the control unit assembly 1 is generally cylindrical, having a diameter D1<40 mm Mechatronic integration is optimized: pump, motor, are integrated optimally in such cylinder.

According to one particular option, the second electrode (32) covers at least the bottom part of the control unit assembly cylinder over at least 130° about axis Z2, over at least 20% of the height H. Seizure of the third contact electrode is therefore particularly convenient, whatever the hand of the user may be (thin, thick, long fingers, short fingers, etc . . . ).

According to one particular option, the control unit assembly and the acoustic sensor are arranged at an angle $\alpha$ comprised between 90° and 140° with regard to the cylindrical configuration of the first cuff portion, as defined in a use configuration on a 30 cm arm perimeter.

It proves to be a particularly convenient and user-friendly spatial arrangement. This is a natural position for having the acoustic waves (4H) sensed against the chest and received by the electronic controller through the acoustic sensor.

The present disclosure is also directed to a system for monitoring cardiovascular parameters, comprising a device as defined above, and a smartphone (85) configured to run an application, which enables the user to enter contextual data and to display at least cardiovascular parameters history for the individual user.

Further, the system may comprise a remote server (86), configured to handle and store a medical file, of at least an individual user.

BRIEF DESCRIPTION OF THE DRAWINGS

Other features and advantages of the disclosure appear from the following detailed description of one of its embodiments, given by way of non-limiting example, and with reference to the accompanying drawings, in which.

DETAILED DESCRIPTION OF THE DISCLOSURE

In the figures, the same references denote identical or similar elements. For clarity purposes, some parts are represented intentionally not at scale with regard to other parts. Also, some parts of timing charts can be represented intentionally not at scale.

Figure 1:
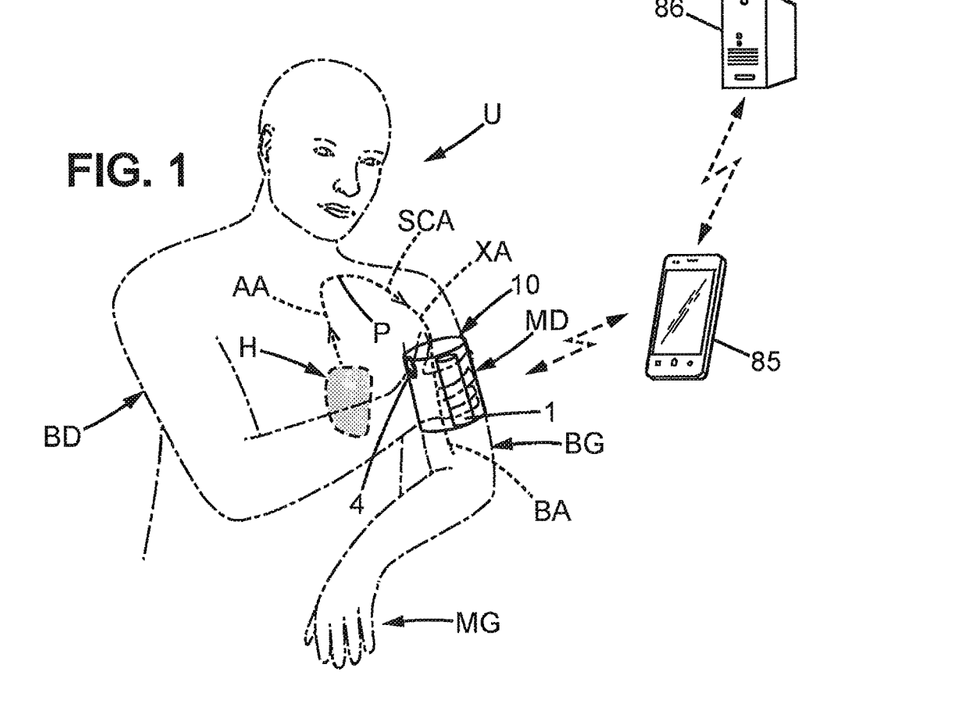
FIG. 1 illustrates a general overview of a device according to the present disclosure in a use configuration.

FIG. 1 shows an individual (also 'user') U in a configuration where he/she is using a device 10 according to the present disclosure. The device (otherwise called "apparatus") 10 looks like a known brachial blood pressure sensing device (commonly named Blood Pressure Monitor i.e. in short "BP Monitor"), but the device exhibits extended functionalities as will be apparent below, so that the device can be called 'upgraded BP Monitor'.

The user U in question has, among other organs and limbs in his/her anatomy: a left arm BG, a right arm BD, a heart H, a left hand MG a right hand MD.

Further the user in question has an aortic artery ('aortic arch') denoted AA, a subclavian artery SCA, an axillary artery XA, a brachial artery BA, belonging generally to the cardiovascular system of the user. Therefore a blood path of interest noted P is defined as the fluid conduit from the heart H to a reference point at the brachial artery BA.

The device 10 has a wireless communication capability to exchange data with a mobile entity like a smartphone 85 (more generally a mobile device belonging to the user U like a tablet, a laptop . . . ). Such smartphone 85 may in turn exchange data with a remote entity like an Internet server 86 (more generally any resource available somewhere in Internet, not excluding a so-called "cloud" resource).

The device 10 has either a small display or no display at all, since the user interface capability provided by the smartphone 85 is fully relevant to support displays relating to the use and extended functionalities of the device.

The device 10 is intended to be used at a home environment, for healthy people as well as people suffering from some disease. It may be used in a medical environment but is particularly suitable to be used by non-medical personnel, i.e. the user under measurement him/herself.

The device 10 comprises an armband 2 wrapped around the arm BG, a control unit assembly 1, and an acoustic sensor denoted 4.

The rest of the time the device is stowed, notably in a folded configuration as will be seen later.

As illustrated on FIG. 1, the device comprises an armband wrapped around the arm i.e. the part of the upper limb comprised between the shoulder and the elbow. However it is not excluded to use the device elsewhere, at the forearm for example.

As illustrated on FIG. 1, the device is installed on the left arm of the user. However it is not excluded to use the device elsewhere, at the right arm for example.

Figure 2:
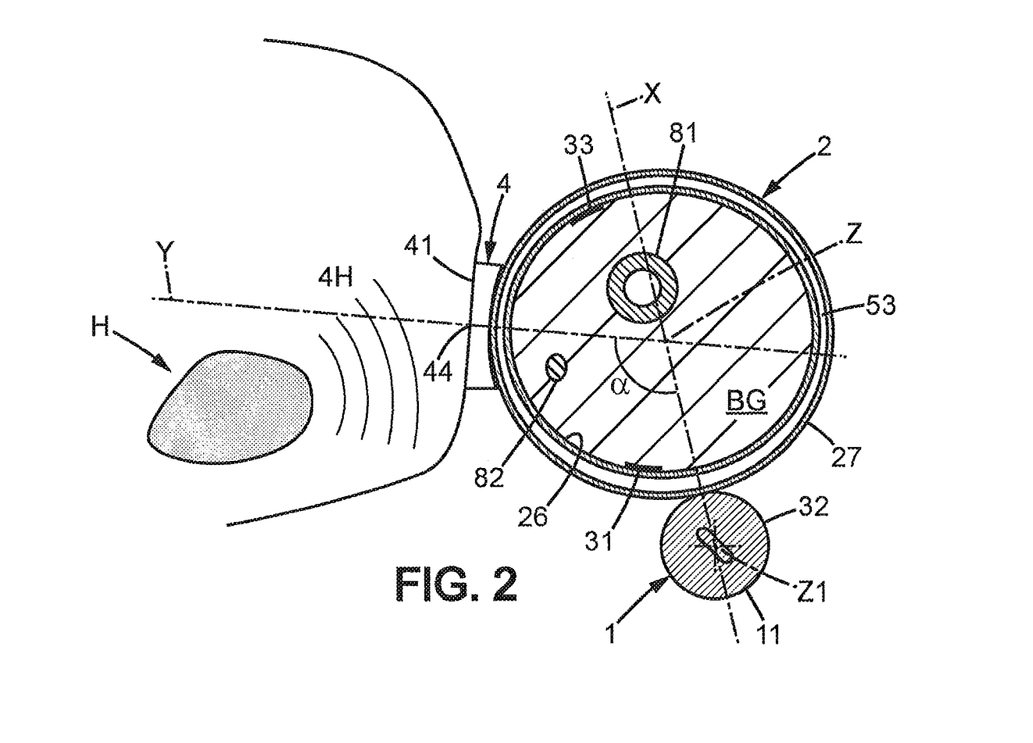
FIG. 2 shows a diagrammatic sectional view of the device in place on the left arm of the user, and adjacent to the chest, for the generically defined embodiment.

As illustrated on FIG. 2, the left arm of the user includes a bone named humerus denoted 81, muscles (not especially shown), and the abovementioned brachial artery denoted 82. The humerus extends along an axis denoted Z. The armband 2, when wrapped around the arm BG, has a general cylindrical shape with a reference axis substantially coinciding with arm axis Z.

The armband has an internal wall denoted 26 intended to contact the arm's skin and to press against the arm. The armband has an external wall denoted 27 on the opposite side of the band with regard to the internal wall 26.

In use configuration, the acoustic sensor 4 is located against the chest, i.e. the left side of chest. Sound waves 4H emitted by the heart are sensed by a sensitive portion 41 of the acoustic sensor 4 the sensitive portion 41 bearing on the left-side chest, i.e. adjacent to the chest. Handling of electrical signals transduced from acoustic waves 4H will be detailed later. It should be noted that acoustic waves 4H can be sensed without trouble through a light clothing, an underwear or the like.

According to one particular option, the device is further equipped with an ECG function, i.e. ElectroCardioGraphic function.

For this purpose there are provided three contact electrodes 31, 32, 33, the three of them integrated in the device, without the need to have linking wires like in most prior art devices.

The first electrode 31 is arranged on the internal wall 26 of the band and has a sensitive face oriented toward the skin of the arm. The third electrode 33 is also arranged on the internal wall 26 and has also a sensitive face oriented toward the skin of the arm.

Each of the electrodes is formed as a thin pad of a surface comprised between 5 cm$^2$ and 10 cm$^2$; a surface between 6 cm$^2$ and 7 cm$^2$ can be chosen; the shape of the thin pad is somewhat curved to follow the standard curvature of the skin of the arm.

In a particular option, first and third contact electrodes 31, 33 are disposed at distance from each other along the circumference. Alternatively, first and third contact electrodes 31, 33 can be arranged differently, for example one above the other or one aside the other.

Whenever the armband is pressurized, first and third contact electrodes 31, 33 are firmly pressed against the skin of the arm, thereby ensuring a fairly good contact with a small electrical contact resistance. It should be noted that no gel is required at the contact electrode contrary to prior art habits. Contact electrodes are to be placed against the bare skin; however, thanks to the pressure, it is not excluded to have a light underwear cloth between the skin and the electrodes.

The contact electrodes can be made of stainless steel, silver, or other coated materials (coated with silver, chromium, gold, titanium or platinum), not excluding materials coated by physical vapor deposition technique (known as PVD techniques).

It is to be noted that two electrodes might be sufficient, therefore the third electrode 33 is considered optional.

Figure 11:
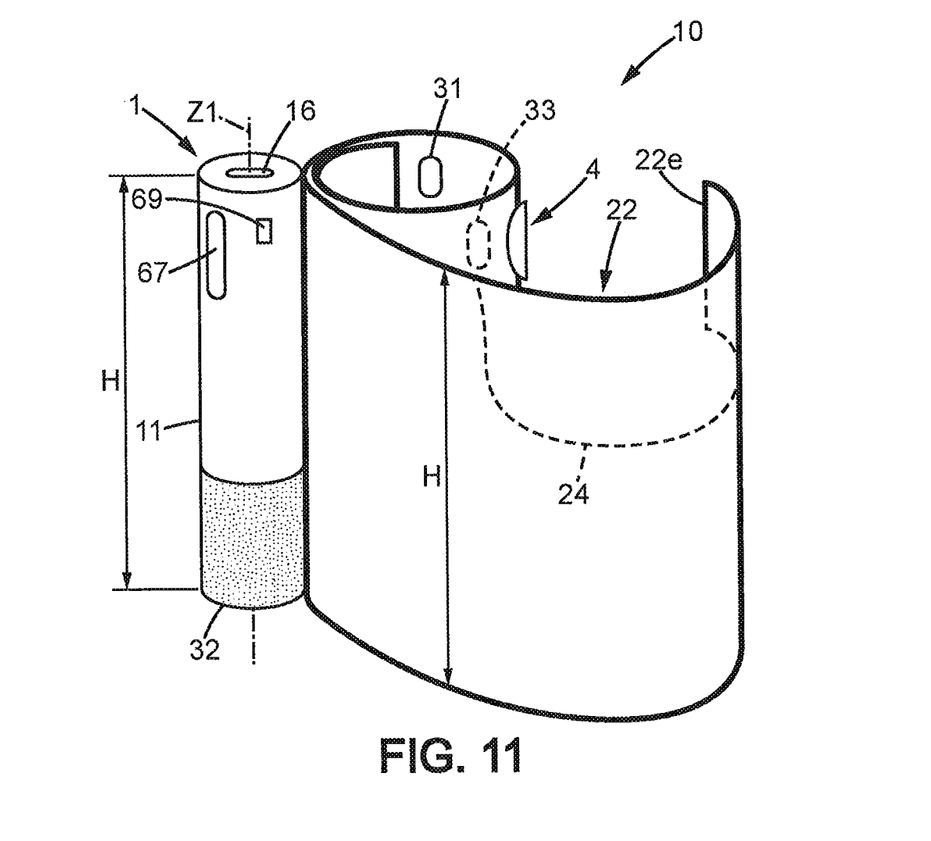
FIG. 11 illustrates a general perspective view of the device of the first embodiment.

Regarding the second electrode 32, it is arranged around the external surface 11 of the control unit assembly as best seen at FIG. 11. A conductive material forms a coating of at least a part of the control unit housing. A metallic coating material (silver, titanium, chromium), are deposited by physical vapor deposition technique (known as PVD techniques).

In one example, the second electrode covers the lower third of the cylinder, for example all around the accessible circumference by the fingers of the user (see FIG. 1). Therefore, it is easy for the user to grab/seize the second electrode with a good electrical contact. According to one example, the second electrode lies over the 20% lower part of the control assembly unit; in other implementation, its height can be bigger, like 30% or 40%.

Figure 4:
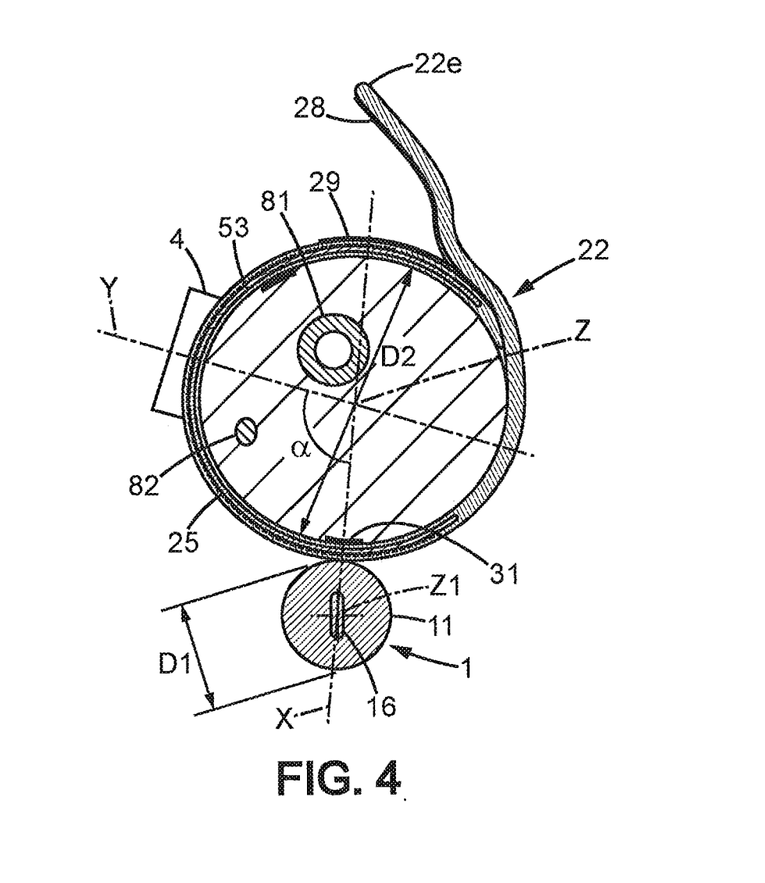
FIG. 4 shows a diagrammatic sectional view of the device in place on the left arm of the user, according to the embodiment shown in FIG. 3.

The above mentioned control unit assembly 1 has, in the shown example, an overall cylindrical shape with an axis denoted Z1 (cf FIGS. 2,4,11). The control unit assembly 1 is fixed to the arm band 2. For example, it is fixed to the first portion 21 as explained below.

As seen on Figures, the general arrangement is as follows: the control unit assembly 1 extends from the external wall 27 of the band with regard to the main axis Z along a direction denoted X. In use configuration, when the chest of the user is nearly vertical, X is substantially horizontal and in a front-rear direction.

In the illustrated case of a cylinder, the diameter of the control unit assembly 1, denoted D1, is less than 40 mm, for example about 30 mm.

The acoustic sensor 4 has a center 44, which is referred to to define the transversal axis Y, extends from the external wall 27 of the band with regard to the main axis Z and passing through the center 44 of the acoustic head. In use configuration, when the chest of the user is nearly vertical, Y is substantially horizontal and in a left-right direction.

Angular distance between axis X and Y is denoted by angle α. In use configuration, the angle α is comprised between 90° and 140°, for example between 110° and 130°. As shown at FIG. 1, in use configuration, the right hand can conveniently seized the control unit assembly 1 and the acoustic sensor is naturally placed against the chest of the user U.

Regarding the acoustic sensor 4, according to one option, it is formed as a piezoelectric transducer, which is able to provide a very thin configuration; this piezoelectric transducer requires very little space projecting from the external wall 27 of the arm band; this piezoelectric transducer requires no electronic supply, just a simple electronic adaptation circuit.

Since the user naturally squeezes the acoustic sensor against the chest, the acoustic sensor can properly work through a thin cloth like a T-shirt, a shirt, even two layers of such cloth.

According to an alternative option, the acoustic sensor can be formed as a microphone.

In FIG. 2, a generic view of the armband is represented; this type of band can be a ring adaptable in diameter/circumference. This kind of band can be inserted from the hand without opening the ring, and slid up to the shown position on the arm. There may be provided restriction means to decrease the play and lock the current position, before pneumatic inflation.

An inflatable bladder 53 is provided. Such a compliant bladder is known per se in blood pressure sensing apparatuses, and therefore not described in details here. At rest, the bladder is arranged within the thickness of the band, as an internal layer.

There may be provided an armature 25, otherwise called cuff holder, for structural support of at least a part of the band. The armature can be an arcuate plastic part, made from a plastic material with good or high mechanical properties (polypropylene, ABS, PVC, or the like), for example having a part-of-a-cylinder shape.

According to one particular aspect, both the bladder 53 and the armature 25 extend circumferentially along the major part of the active portion of the armband 2; such that in use, the bladder is surrounding practically all the circumference of the arm of the user. Therefore, a homogenous pressure is applied all around the arm which is beneficial for the accuracy of the measurement and the quality of the contact of the ECG electrodes 31, 33.

Figure 7:
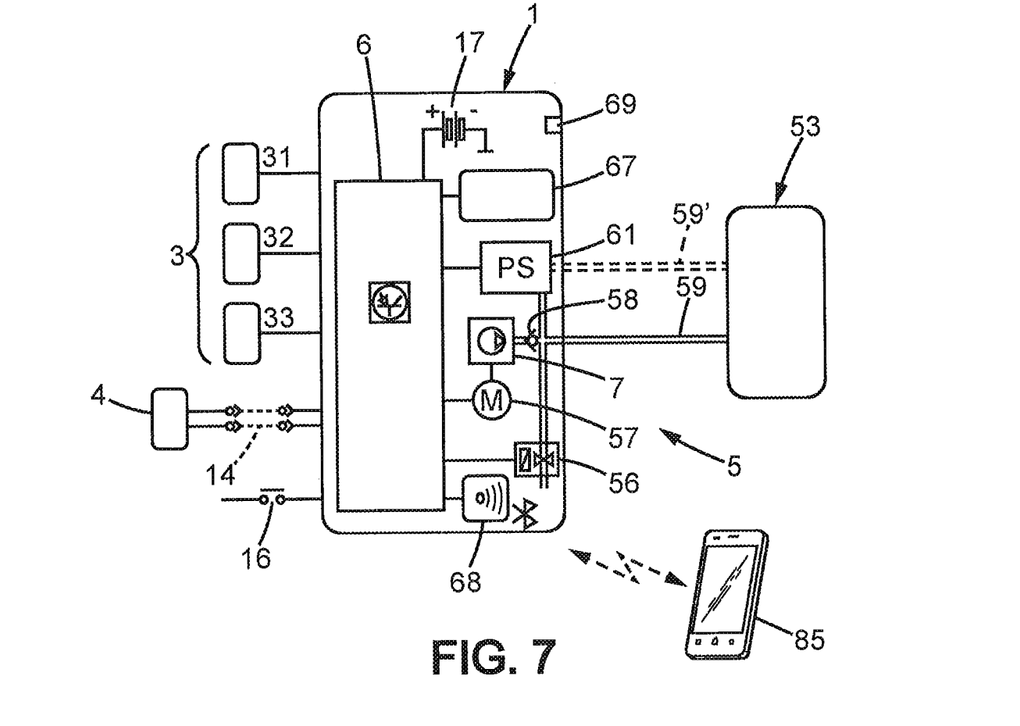
FIG. 7 shows an illustrative block diagram of the device.

As visible on FIG. 7, the control unit assembly 1 comprises a battery 17, an electronic controller 6 and a pneumatic unit 5. We note that no external wired connection is needed.

The pneumatic unit 5 comprises at least a pump 7 driven by an electric motor 57, a release valve 56 also called "bleeder valve" 56, and a pressure sensor 61.

The pneumatic unit 5 may optionally comprise a check valve 58. The release valve 56 may be an On/off valve or a proportional valve.

Additionally, there may be provided a leakage valve.

The control unit assembly 1 comprises an On/Off switch 16; This switch 16 can be a conventional press switch, it can also be a capacitor or touch switch. There can be provided also a tap actuation function using an embedded accelerometer.

The user may start a measurement, after having installed the armband, by actuating the switch 16.

The device is supplied by a battery 17; said battery is for example a rechargeable battery; said battery can be of the Lithium Ion type.

Further the control unit assembly 1 may further comprise a wireless interface 68 such as for example a wireless coupler (WiFi, Bluetooth™, BLE or the like), and a display 67 already mentioned. The display 67 can be a LED display and or a dot matrix display; on this display, blood pressure results can be displayed directly without use of the smartphone application.

There may be provided a pneumatic hose 59 to fluidly connect the output of the pump to the bladder. It can be a one-way pneumatic connection or a two-ways pneumatic connection (59, 59'). According to one variant, there is provided a specific sense line 59' decoupled from the preservation line 59.

According to a particular embodiment, the bladder 53 is connected to the pneumatic unit by an integrated pneumatic connector 55.

Figure 12:
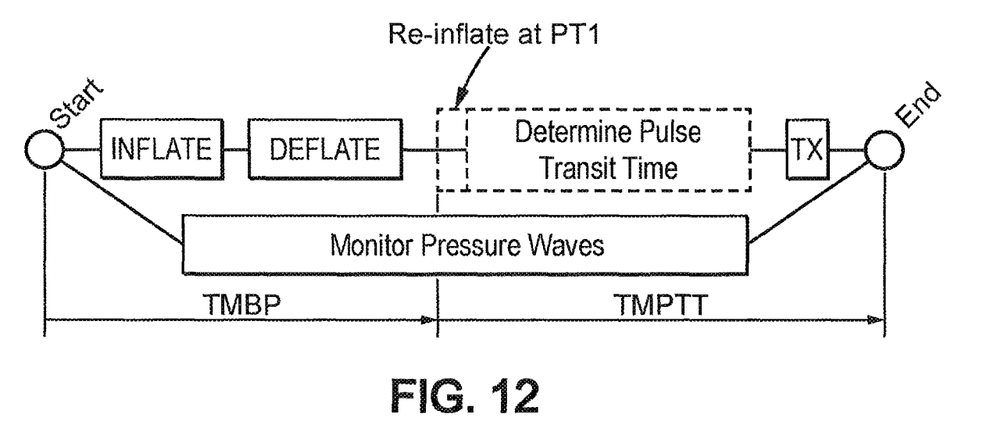
FIG. 12 illustrates a general overview of the disclosed method.

A first overview of the functionality of the device is given here, whereas it would be described later in more detail with the help of FIGS. 9 and 12.

A blood pressure measuring cycle is carried out first, and optionally, thereafter a pulse transit time PTT measuring cycle is carried out. In the same timeframe or separately, individual ECG signal analysis and/or phonocardiogram signal analysis can also be performed.

For the blood pressure measuring cycle, the electronic controller 6 is configured to first inflate the inflatable bladder 53 until the blood flow is greatly reduced by the pressure exerted on the arm. During inflation, the analysis of the evolution of pressure signals allows to infer the systolic pressure and the diastolic pressure. The controller is configured to then progressively deflate the bladder 53. The progressive reinstatement of the blood pressure waves is also analyzed by the electronic controller 6 to infer the systolic pressure and the diastolic pressure, in confirmation or replacement of values deduced during the inflation phase.

Regarding the pulse transit time PTT, the electronic controller 6 determines a first characteristic instant and a second characteristic instant, and the resulting time difference is used to calculate a pulse wave velocity to finally issue an index representative of the arterial stiffness to the user.

Now are described in detail embodiments and variants of the device structure.

According to the first embodiment, illustrated at FIGS. 3, 4, 10 and 11, the band 2 comprises a first portion 21 and a second portion 22. The first portion 21 can be considered as the main portion since the control unit assembly 1 and the acoustic sensor 4 are affixed to this first portion 21, and furthermore this first portion houses the inflatable bladder 53, and optionally, the structural elastic armature 25 already mentioned.

Figure 3:
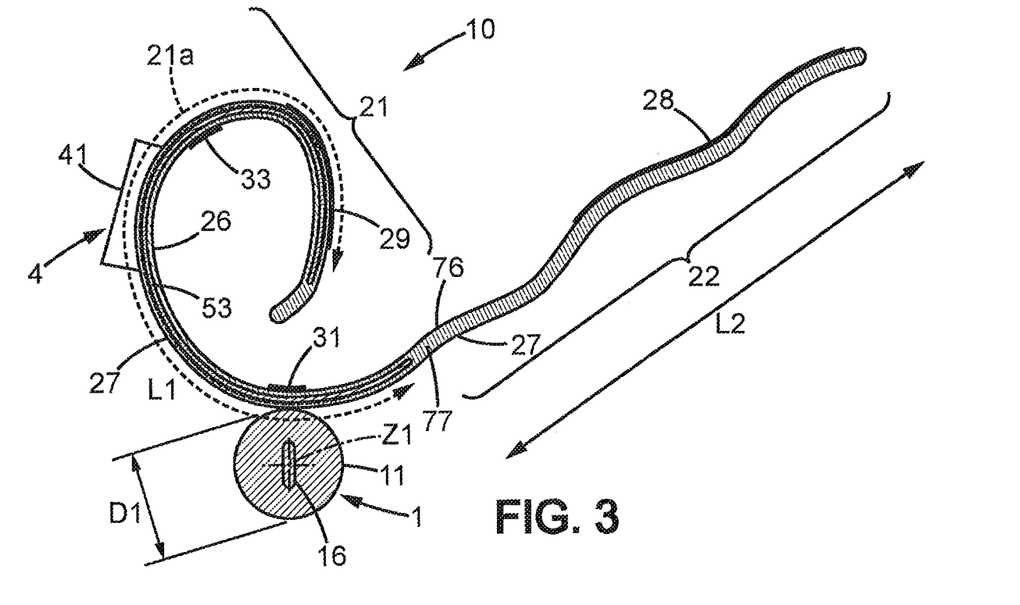
FIG. 3 illustrates a mechanical configuration of the device in an open configuration, according to a first embodiment.

The first portion 21 has a developed length denoted L1. The second portion 22 has a developed length denoted L2. The band has a height H. Likewise, the armband 2 is made from a generally rectangular shape with a width corresponding to dimension H and a length corresponding to added dimensions L1+L2.

Figure 10:
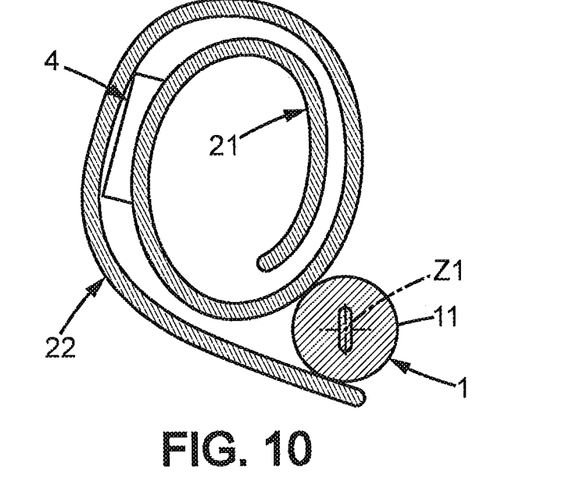
FIG. 10 illustrates the mechanical configuration of the device of the first embodiment in a stowed configuration.

For installing the arm band 2 around the arm prior to inflating, the user starts for example from a stowed configuration depicted in FIG. 10, the user unrolls the second portion 22 (see FIG. 3) to make it possible to install the first portion around his/her left arm BG. Thanks to the elasticity of the first portion, the first portion 21 can be opened so as to facilitate the insertion of the arm into the internal space encompassed by the first portion. The user has to move away a little bit his/her arm from the chest to do that.

It should be noted that this configuration allows installing the band/cuff without inserting it along the forearm from the hand side.

Further operation involves the closing of the band 2 around the arm, and securing this configuration prior to inflation.

A hook pad 29 is arranged at the external wall of the first portion 21 and a corresponding loop pad 28 is arranged at the internal wall of the second portion 22. Of course the reverse configuration loop/hook is also possible.

Regarding the dimensions, the hook pad 29 extends for example along all the height H over a length of 5 cm to 10 cm; the loop pad 28 is longer, it also extends for example along all the height H but over a length of 10 cm to 20 cm.

After the user has placed the first portion 21 around the arm on the side of the chest as described before, he/she pulls the second portion 22 toward the rear direction and then sticks the second portion 22 onto the first portion 21 by securing the loop pad 28 on the hook pad 29. The remaining unused end 22e of the second portion is left free (FIG. 4).

Alternatively, according to a variant illustrated at FIG. 11, where a special cutout 24 is provided, the remaining unused end 22e of the second portion can be folded around back into the front direction.

FIG. 4 shows the device ready for inflation, the user presses the device onto his/her chest to guarantee acoustic adaptation.

In use configuration, the angle α is comprised between 90° and 140°, for example between 110° and 130°, which provides a very natural installation of the device with the acoustic sensor placed in the ideally against the left side of the user's chest.

It should be noted that the length of the second portion together with the length of the hook pad and the length of the loop pad allows the device to be adjusted to a large variety of arm circumference and diameter D2.

Figure 5:
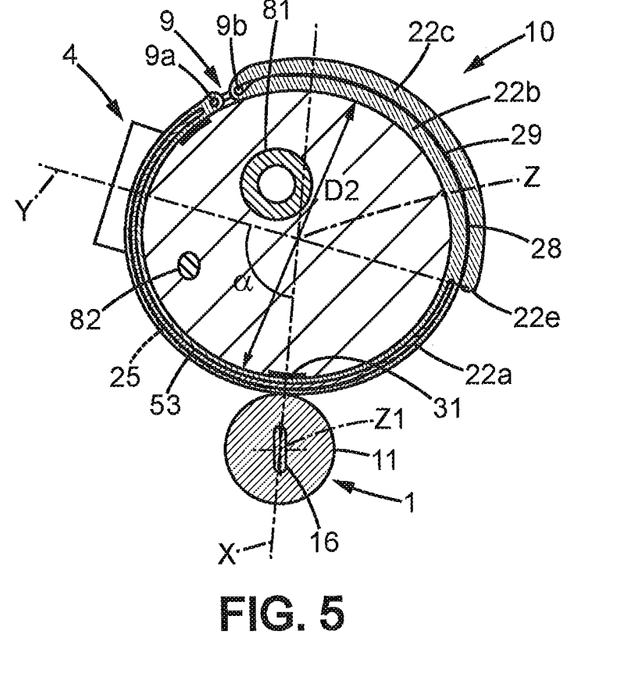
FIG. 5 shows another diagrammatic sectional view of the device in place on the left arm of the user, according to a second embodiment.
Figure 6:
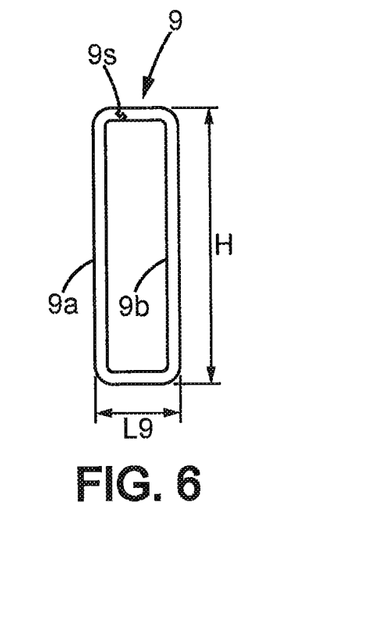
FIG. 6 illustrates a buckle configured to be used in co-operation with the arm band, according to the second embodiment

At FIGS. 5 and 6, a second embodiment of the armband is represented, which also allows to install the band/cuff without inserting it from the hand. Again, the band 2 comprises a first portion 21 and a second portion 22.

In this embodiment, the device also comprises a buckle 9, also named 'return buckle' as seen on FIG. 6. The buckle can be manufactured as a bent metallic wire, shaped as a rectangular loop. The buckle can also be made from plastic material with good or high mechanical properties. Two long sides 9a, 9b are connected at their respective ends by two small sides, thereby forming a rectangle with a length/height H and a width denoted L9.

The buckle is fastened to one circumferential end 21a of the first portion 21, at complete opposite from the other end 22e of the band 2.

For the assembly of the buckle on to the end 21a, it can be provide a seam in the band end, done after insertion of the loop buckle. Alternatively, the loop formed by the buckle may have an openable slit 9s, with self locking retaining means (hook and/or the like).

For installing the arm band 2 around the arm prior to inflating, the user places the first portion 21 around the arm on the side of the chest and passes the second portion 22 into the buckle 9 toward the rear and then pulls the end of the second portion 22 toward the front direction, until the arm wraps the arm without substantial play. Then the user sticks the returning portion 22c against the base 22b of the second portion to attach the attachment means, which results in the configuration shown at FIG. 5.

Figure 15:
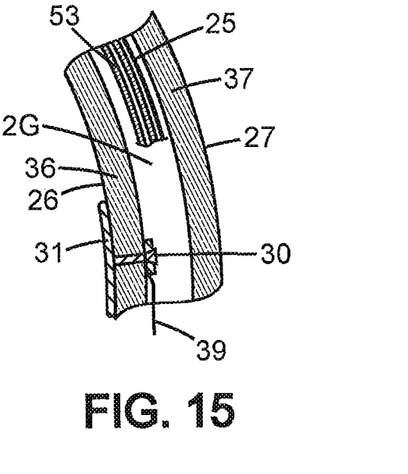
FIG. 15 shows a detailed sectional view of the armband.

According to an aspect which is common to all embodiments, at least in part of the band, as shown at FIG. 15, the band 2 comprises an internal layer 36 and an external layer 37 with an interval 2G available between the two layers. In the gap 2G, there may be provided the bladder 53, the armature 25, rivets 30 for fastening the contact electrode 31 and a connection wire 39. Other wires may be present, for connecting the acoustic sensor to the electronic controller 6, and the third electrode.

There may be a single layer portion (i.e. without gap or interval), notably in the distal end of the second portion 22.

The band 2 is for example made of strong fabric, woven or non-woven or synthetic material.

Generally speaking, the band 2 comprises attachment means, for fixing the size of the armband prior to inflating. The attaching means may comprise one or more couple(s) of loop and hook pads.

Therefore, a 'continuous' unquantitized adjustment of encompassed circumference is made available, for any size of arm.

It should be noted that in the present specification, arm circumference CIRC or diameter D2 are indifferently used, since we know that CIRC=π×D2.

According to other possible solutions, there may be provided attaching means including a releasable ratchet system, or a teeth system.

Regarding dimensions, the following preferences can be noted.

For a baseline device intended to encompass arms having a perimeter/circumference CIRC comprised between 20 cm and 42 cm, which represents most of the users:

L1 is for example comprised between 20 cm and 32 cm.
L2 is for example comprised between 15 cm and 25 cm.
H is for example comprised between 12 cm and 16 cm.

For an XXL device (special large dimension variant) intended to encompass arms having a perimeter CIRC comprised between 40 cm and 62 cm:

L1 is for example comprised between 40 cm and 45 cm.
L2 is for example comprised between 20 cm and 25 cm.
H is for example comprised between 14 cm and 18 cm.

This XXL variant can have a frusto-conical configuration, smaller diameter at the elbow oriented end.

When the device is unused, as illustrated at FIG. 10, it can be rolled up, whereby its size is less than 10 cm×10 cm×H.

In the variant illustrated at FIG. 11, the second portion 22 of the armband can exhibit a smaller height for its most distal area; this option is delineated by the dotted line 24; in this case, when the free end 22e of the second portion is wrapped around the first portion at the location of the acoustic sensor, the acoustic sensor 4 is still uncovered by the second portion. Therefore, even though the user installs the device by wrapping it all around, this won't prevent the device from working regarding the acoustic acquisition against the user's chest.

Figure 16:
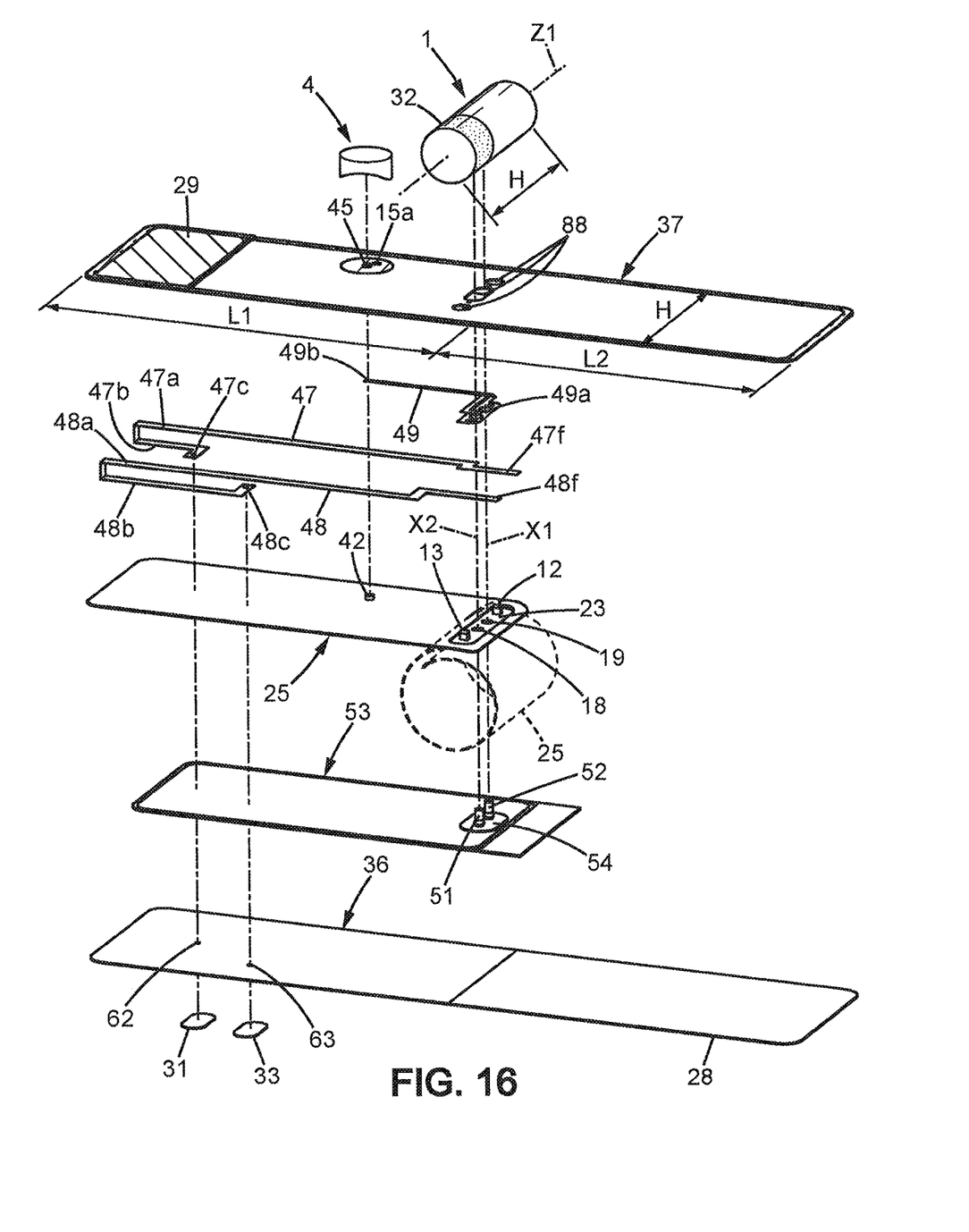
FIG. 16 shows an exploded view of the device.

As illustrated at FIG. 16, the general architecture of the device 10 is better understood by contemplating the exploded view. From bottom to top, we find the internal layer 36 of the armband 2 together with the contact electrodes 31, 33. The left side of the FIG. 16 corresponds to the first portion 21 of the armband (length L1), whereas the right side of same figure corresponds to the second portion 22 (length L2).

The face (internal wall 26) which is to be in contact with the arm of the user is the underside at the left. The right underside of internal layer 36 carries a loop pad 28 as already mentioned above.

Atop the internal layer 36, at the left side, there is provided the bladder 53. The bladder is fitted with a pneumatic connector 54 having a flat base and two tubes 51, 52, corresponding to pneumatic connection 59 (two ways variant with 59') at FIG. 7.

Atop the bladder 53, at the left side, there is disposed the armature 25, which is shown in dotted line at its rest configuration, whereas shown in flattened configuration in solid line The resilient armature 25 comprises a rigid socket 23 fitted with various interface elements for connecting the armature to the control unit assembly 1. Among interface elements, there are provided two holes 18, 19 in which pneumatic connector sleeves pass. There are also provided two clamping protrusions 12 13 designed to be inserted in respective snap recesses in the housing of the control unit assembly 1.

The resilient armature 25 comprises a locating pin 42 for mechanically receiving the acoustic sensor.

Atop the resilient armature 25, there is shown to conductive flexible tracks 47 48, which form the major part of the electrical connection between the contact electrodes 31 33 and the control unit assembly 1.

It should be noted that this conductive flexible tracks go at the far left 48a 47a and there turn around the armature 25 and the bladder 53 and the return sections 48b 47b are therefore located between the bladder and an internal layer 36. At the end of the conductive flexible tracks there are provided perforations 48c 47c such that rivets 30 can be inserted to fasten each of the electrode. There may be provided perforations 62 63 in the internal layer 36 at the position of the rivets.

It should be noted that the gap between portions 47a and 47b (respectively between 48a and 48b) has been exaggerated.

The right ends 47f 48f of the conductive flexible tracks lies below the control unit assembly where electrical connection is arranged.

There is provided a third electrical connection 49, which form the major part of the electrical connection between the acoustic sensor 4 and the control unit assembly 1.

This connection can be formed as two-wire flexible cable.

One end 49a is connected to the control unit assembly, more precisely to the electronic controller 6, the other end is connected to either directly to the acoustic sensor, or in an alternate fashion to a connector 15a, to which can be connected the acoustic sensor 4.

Atop the resilient armature 25 and the electrical connections, we find the external layer 37, which has a size H×(L1+L2) corresponding to the size of the internal layer 36.

The external layer comprises, at the far left, the hook pad 29, a plurality of holes 88, which form passages for the two fluids conducts and for the electrical connection towards the control unit assembly. A perforation 45 is arranged at the position of the pin 42.

Finally, at the top level, the control unit assembly 1 comprises clamping recesses to receive the clamping protrusions 12 13, a pneumatic socket to receive the air sleeves 51, 52.

The internal leader and the external layer are assembled together by welding, although seaming is not excluded. Doing that, the other components mentioned above are taken in a sandwich configuration.

The device works as follows.

During a measurement, the patient's heart generates electrical impulses that pass through the body at high speed. Also simultaneously the patient's heart generates acoustic waves that pass through the body with a certain sonic speed.

These impulses/waves accompany each heartbeat, and the heartbeat generates a pressure wave in artery network that propagates through the patient's vasculature at a significantly slower speed. The blood path P of interest has a certain length, let's say 30 cm to 40 cm according to the physical characteristic of the individual under measurement. As will be seen in more detail later, this length depends at first order on user's height denoted UH.

Immediately after the heartbeat ventricular contraction, the pressure wave leaves the heart and aorta, passes through the subclavian artery, to the brachial artery along the path P.

The ECG electrodes measure electrical signals which pass to an amplifier/filter circuit within the control unit assembly. For example, a filtering circuit is provided before the signal is digitized and entered into the microcontroller.

Within the controller, the signals are processed with an analog-to-digital converter to form the ECG digitized waveform and then recorded together with the time of occurrence, namely instant T0. ECG waveform is named "QRS waveform" or "QRS complex" as sample shown at FIG. 8.

The acoustic waves are also band-pass filtered and amplified, for example after upfront digitalization. A bandpass filter with cutting frequencies [0.5 Hz-1 kHz] is applied, either in the analog font end before digitization or applied to the digitized acoustic signal.

Figure 8:
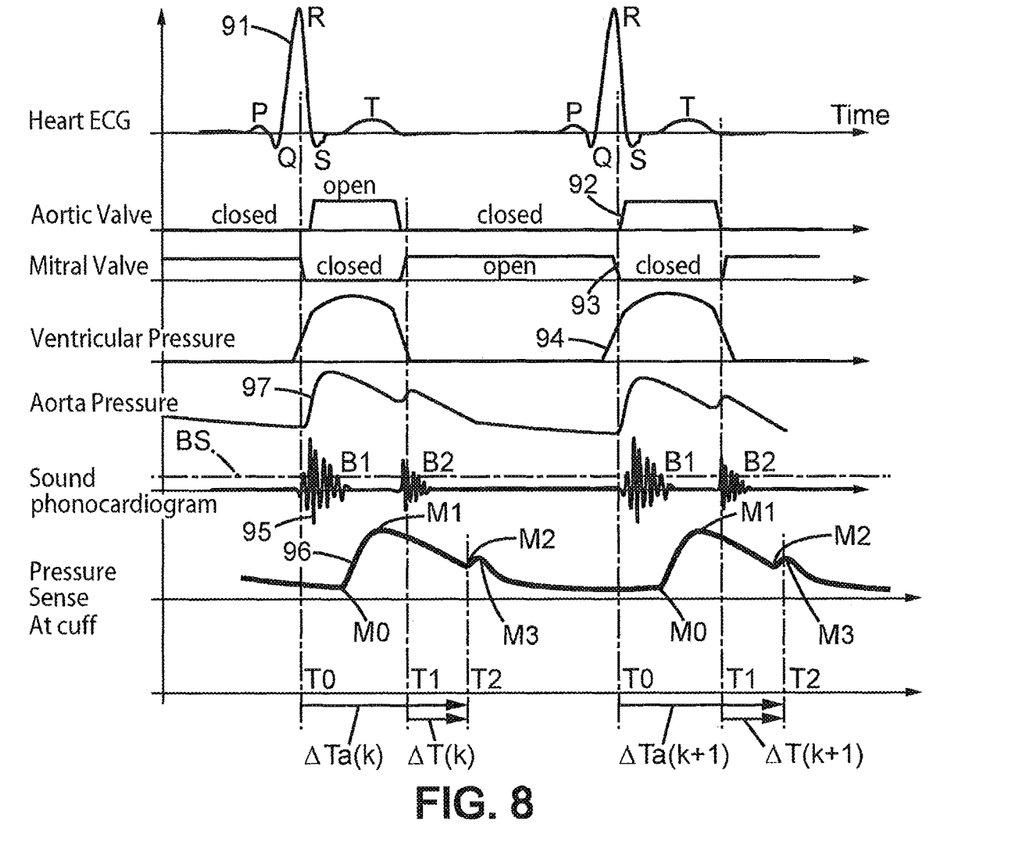
FIG. 8 shows a timing chart illustrating the method, at the heartbeat timescale.

"QRS waveform" 91 is the top curve shown on timechart at FIG. 8. This waveform is known per se thus not described in details here. Instant T0 corresponds in the illustrative embodiment to R apex, but another marker can be taken alternately.

Aortic valve open/close state is also shown just beneath, signal denoted 92.

Mitral valve open/close state is also shown just beneath, signal denoted 93.

Just before aortic valve opening, the mitral valve closes; this produces a particular sound which is reflected in the first significant sound named B1 as shown on curve 95.

Further, after closing mitral valve and opening aortic valve, the ventricular volume decreases as blood is ejected to the aorta. At the same time ventricular pressure 94 exhibits a rounded apex. Aortic pressure curve is shown and denoted 97.

Sound phonocardiogram corresponds to curve denoted 95 electrically reflects waves received at the acoustic sensor 4.

This curve 95 exhibits two characteristics sounds; the first sound denoted B1 corresponds to the closing of the mitral valve, the second sound denoted B2 corresponds to the closing of the aortic valve.

A "significant sound", in the sense of the present disclosure, is defined whenever a instantaneous power of the acoustic signals exceeds a predetermined threshold (BS), cf FIG. 8.

It should be noted that sounds B1 and B2 exceeds BS threshold.

Pressure wave at pressure sensor 61 in fluid communication with bladder 53 is shown at curve 96.

This curve 96 exhibits three characteristics apexes. The first apex denoted M1 is a maximum apex; the second apex denoted M2 is a minimum local apex; the third apex denoted M3 is a maximum local apex.

Besides M0 is the minimum value, just before the rise which is a consequence/response of the arrival of the pressure pulse at the arm.

The second apex denoted M2 is a marker corresponding to arrival of the effect of the closure of aortic valve at the brachial artery within the arm band.

There may be defined a reference point in the arm, so that the ideal position for the device can be notified to the user, for example distance from the elbow internal fold, or another criterion.

Generally speaking, for the purpose of PTT, T1 is defined as the instant of the maximum instantaneous signal power of the second sound B2 reflecting when aortic valve closes.

Generally speaking, T2 is defined as the instant when second apex denoted M2 occurs.

Blood Pressure Procedure (BP Procedure)

Figure 9:
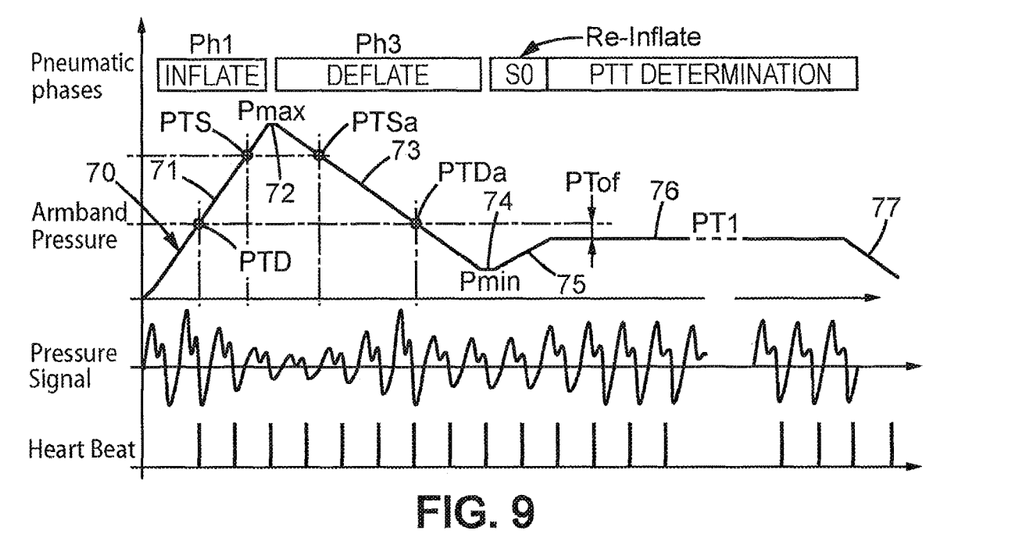
FIG. 9 shows a timing chart illustrating the method at a larger timescale.

This procedure is known in the art, and thus it is not described in details here. Basically, it comprises the following phases:

Ph1—start inflating the bladder, inflation phase is denoted 71 at FIG. 9,
PhD—determining Diastolic Blood pressure (PTD) during inflating phase
PhS—determining Systolic Blood pressure (PTS), during inflating phase
Ph2—stop inflating the bladder 72 (when hardly no more pressure wave is identified),
Ph3—start deflating the bladder, deflation phase is denoted 73
PhS—determining Systolic Blood pressure (PTSa), during deflating phase
PhD—determining Diastolic Blood pressure (PTDa) during deflating phase More precisely, the shape of the pressure waves are analyzed by the electronic controller. During inflation 71, as shown at FIG. 9, the shape of the pressure waves evolves, and a predefined criteria on the waveform makes the decision to record a first diastolic blood pressure PTD, and another set of predefined criteria on the waveform makes the decision to record a systolic blood pressure PTS.

In a similar fashion, during deflation phase, the shape of the pressure waves are analyzed by the electronic controller. During deflation 73 the shape of the pressure waves evolves, and a predefined criteria on the waveform makes the decision to record another systolic blood pressure PTSa, and another set of predefined criteria on the waveform makes the decision to record another diastolic blood pressure PTDa.

PTT Procedure

This procedure is adapted to determine as accurately as possible the pulse transit time PTT.

It comprises the following phases:
/S0/—inflate 75 the bladder at a predetermined pressure denoted PT1, the inflation bringing the pressure from the lowest value 74 to this predefined level PT1, detailed below
/S1/—determining the above-mentioned aortic valve closing instant T1($k$) from acoustic signals,
/S2/—determining subsequently, from pressure signals, a characteristic point (M2) of the pressure signal curve occurring at instant T2($k$),
/S3/—calculate a time difference, defined as $\Delta T(k)=T2(k)-T1(k)$ The predetermined pressure PT1 can be defined as a function of PTD, for example with a value below the diastolic pressure PTD; this value may be defined by a predefined offset PTof; in other words, PT1 can be such PT1=PTD−PTof, with PTof for example equal to 10 mmHg (10 Torr).

According to one option, said characteristic point (M2) is the above-mentioned local minimum apex, after first apex M1.

Further, steps S1 to S3 are repeated until a stop criterion SC is met. This stop criterion SC can be defined according to different possibilities. One consists in a predefined duration. Another one consists in counting the number N of heartbeat cycle; for example N is chosen between 4 and 20.

Overall duration for BP procedure is denoted TMBP and duration for pulse transit time procedure is denoted TMPTT. For example TMBP is less than 10 seconds. For example TMPTT is less than 12 seconds. According to a user configuration, selectively chosen by user through the smartphone or locally by a double press on the switch 16, the user can choose to carry out only the blood pressure or BP procedure plus PTT procedure.

During PTT procedure, pump is not energized and a bleeder valve comprised in the pneumatic unit is not energized. Therefore, no intrinsic parasitic noise disturbs the PTT procedure.

The electronic controller 6 computes therefrom a time difference, defined as
$\Delta T(k)=T2(k)-T1(k)$ for the heartbeat arbitrarily numbered k.

PWV is the wave velocity along path P.
PWV is defined as PWV=length(P)/$\Delta T(k)$ In practice, we prefer to rely on a successive series of N measurements; in this condition, the method may comprise the following:
S41—calculate an average value $\Delta Tav$ of $\Delta T(k)$, for k=j to j+N
S42—calculate a Pulse Wave Velocity (PWV) defined as PWV(k)=length(P)/$\Delta Tav$, The number N of effective PTT measurement can be chosen between 4 and 16.

The average value can be computed as follows $$\Delta Tav = \frac{1}{N}\sum_{k=j+1}^{k=j+N}\Delta T(k).$$

The height (UH) of the user is taken into account at step S42, namely length(P)=F1 (UH)

Also age (UA), gender (UG), and weight (UW), of the user may additionally be taken into account at step S42, namely length(P)=F2 (UH, UA, UG, UW).

Arterial stiffness AS can be defined as a function of PWV. AS can be expressed as a rating between 1 and 10; it can also be expressed as an equivalent age of the person.

A plurality of subsequent evaluations of Pulse Wave Velocity are recorded for a particular user to form a history curve displayed at the smartphone 85, and a deviation in said curve is notified to said particular user.

It should be noted that the disclosed device has complete power autonomy; According to a particular option, the device is formed as an integral unit, there is no external wire, not external hose, style and practicality are enhanced.

The control unit assembly 1 can have a different shape than the cylinder, it could be formed as a square profile, oblong, etc . . . .

Figure 13:
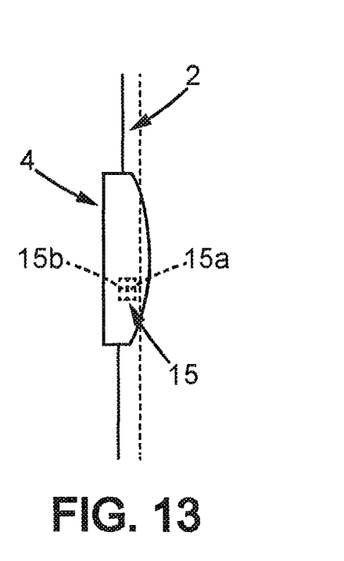
FIG. 13 shows a detailed view of the acoustic sensor in its docked position.

According to a particular option, the acoustic sensor 4 can be detachable from the main unit. FIG. 13 shows the default position, namely the docked position, when the acoustic sensor is plugged and fixed to the external wall 27 of the armband 2. There is an internal connection between a base connection be noted 15*a*, and a complementary connector 15*b* belonging to the acoustic sensor itself. This connection can for example be a Micro USB connection.

The detachable acoustic sensor 4 can be of a wired type or of a wireless type.

Figure 14:
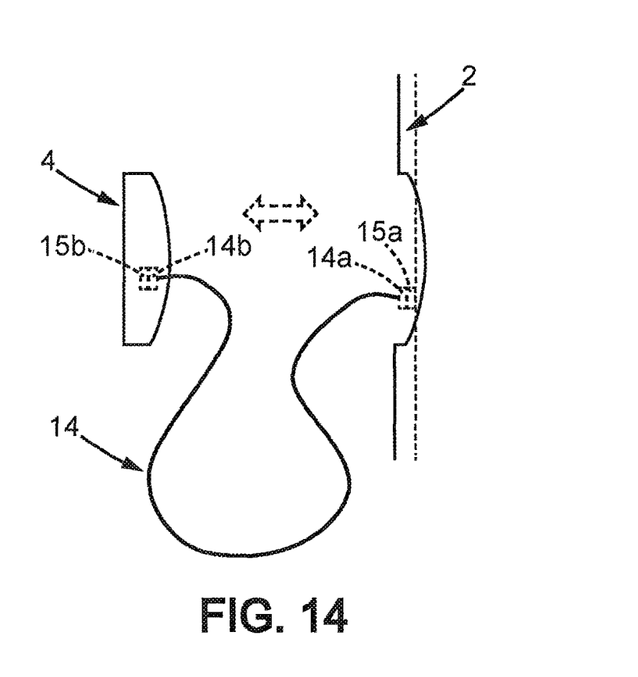
FIG. 14 shows a detailed view of the acoustic sensor in a detached position together with the extension cable.

In the case of the wired type, together with the device 10, there may be provided an auxiliary cable denoted 14, also called extension cable or extension cord. At one end of this cable, there is provided a connector 14*a* counterpart of the base connector 15*a*; at the other end, there is provided a connector 14*b* counterpart of the on-board connector 15*b*. The extension cable comprises two wires. More wires are not excluded.

In the case of the wireless type, the detachable acoustic sensor includes a battery and the Bluetooth™ wireless interface, through which the detachable sensor can send sensed signal to the electronic controller 6. When docked onto the arm band, the onboard battery can be recharged by the 'main' battery of the control unit assembly.

FIG. 14 shows the detached position, in which the acoustic sensor 4 can be placed on the chest of the user at different positions, like a move-around satellite of the main unit. In this configuration, it is possible to organize a telemedicine sequence, since the electronic controller is connected to the smart phone, and the smartphone into is connected to the Internet. Some early diseases of heart valves can be thereby diagnosed by a physician located remotely from the user's premises. Recommended auscultation spots/sites can be shown to the user in the smartphone application.

Additionally, but not necessarily, there may be provided an auxiliary acoustic sensor (not shown) on the internal wall of the armband and oriented toward the arm; such that this auxiliary acoustic sensor can detect Korotkoff sounds during decrease of the applied pressure.

Summary of Cardiovascular Parameters/Functions That Can be Monitored by the Device As already mentioned, Diastolic blood pressure PTD, and systolic blood pressure PTS can be obtained from the blood pressure procedure, as a motion of blood pressure cuff.

Also, as described before, PTT procedure allows to determine the arterial stiffness.

Also, heart rate HR can be inferred from ECG signals 91 from phonocardiogram signals 95, or from oscillometric signals 96, by measuring the average time separation between two heartbeats and deducing therefrom the number of heartbeat and minute.

Also, the device can perform ECG signal analysis, for detection of arrhythmia, as known per se. Some anomalies in ECG signal 91 can be identified and associated to a type of arrhythmia, such as arterial fibrillation.

Also, the device can perform a phonocardiogram analysis for detection of heart anomalies responsible for so-called heart murmurs. In particular, some anomalies in phonocardiogram signal 95 can be identified and associated to a valvulopathy, concerning any of the mitral, tricupside, aortic, or pulmonary valves.

ECG analysis and phonocardiogram analysis can be carried out simultaneously with the PTT procedure, or separately, namely before or after PTT procedure. ECG analysis can be performed all along and at any time whereas phonocardiogram analysis is for example carried out when no intrinsic source of noise is present.

System, Application and Remote Patient Monitoring

The user can follow his/her own metrics on a smartphone application.

The device can be used by more than one user, selection of relevant user can be done through the local display 67 or through the smartphone application. When actuated, directly on the device, the activation switch 16 can be used to scroll across several users names.

There is provided a Micro USB connection 69 for battery recharge and for downloading of data.

The smartphone application can display a history of measurement reports, which can include ECG signals, phonocardiograms.

It should be noted that phonocardiogram can be replayed via the smartphone application and the loudspeaker/headphones coupled to the smartphone.

Smartphone application can issue time reminders for the user, so the user can measure cardiovascular parameter regularly with the integrated device 10.

The integrated device 10 is configured to send an alert to the physician whenever some particular thresholds are exceeded or when particular events are detected, such as an episode of arrhythmia. Such thresholds regarding blood pressure can be defined either by the user him/herself or by the physician/doctor.

The user can add the contextual note(s), such as medicine intake or a life circumstance (just after wakeup, just before going to bed), to one or more measurement reports.

Measurement reports can be sent remotely to a server that can be accessed by the physician/doctor, so that the physician can analyze the patient's data from a distant location.

The system allows remote analysis of ECG signals; the user can receive in return the diagnostic from the physician.

System Including an Emectronic Scale and the Above Mentioned Blood Pressure Monitor 10

The present disclosure is also directed to a personal health system, which includes an electronic scale as disclosed in EP3095380 and the Blood Pressure Monitor 10 as disclosed above. From time to time (for example once a week to give an idea, or every 3-4 days), the user makes use of the blood pressure monitor, and therefore, a conventional measurement of the user's blood pressure is performed together with a measurement of the brachial pulse transit time; such data is uploaded and stored in the smartphone application and/or remote server under the user personal data logger.

On a more frequent basis (for example every morning), the user makes use of the electronic scale, which besides the weight measurement performs a measurement of an auxiliary pulse transit time (taken at the foot/feet).

Therefrom, daily measure of auxiliary pulse transit time (with scale) allows to compute after each weighing sequence a calculation of a relative correction to apply to the conventional blood pressure.

The user can be notified of its current blood pressure which is determined to be the latest conventional blood pressure corrected by the relative correction of the day.

The invention claimed is:

1. A device for collecting cardiovascular data relating to an individual user, comprising:
   an arm band having an inflatable bladder and an internal wall, and configured to surround an arm of the individual, with the internal wall in contact with the arm's skin,
   a housing having a cylinder shape extending along a main axis, the housing receiving an electronic controller and a pump configured to inflate and deflate the inflatable bladder, and wherein the electronic controller is configured to control the pump
   a set of contact electrodes for electrocardiographic sensing, the set of contact electrodes including at least first and second contact electrodes for electrocardiographic sensing, the first electrode being arranged in the internal wall of the arm band, the second electrode being arranged at an external wall of the housing, wherein the second electrode covers at least a bottom part of the cylinder shape of the housing over at least 130° about the main axis and over at least 20% of a height of the housing.

2. The device according to claim 1, wherein the arm band comprises a first portion which has a structural resilience and a second portion which is formed as a flexible extension of the first portion, and fitted with an attaching means.

3. The device according to claim 2, wherein the attaching means comprise loop and hook pads, a loop pad at one location and a hook pad at another location, such that adjustment and securing of various encompassed circumferences ($\pi D2$) of the arm is made available.

4. The device according to claim 2, wherein the housing and the first and second portions have substantially the same height.

5. The device according to claim 2, wherein the set of contact electrodes comprises a third contact electrode, arranged in the internal wall of the first portion of the arm band.

6. The device according to claim 1, further comprising a display.

7. The device according to claim 1, wherein the device forms an integral unit.

8. The device according to claim 1, wherein the housing is has a diameter $D1 < 40$ mm.

9. A system for monitoring cardiovascular parameters of an individual user, comprising a device as defined in claim 1, and a smartphone configured to run an application configured to enable the user to enter contextual data and to display at least cardiovascular parameters history for the individual user.

10. The device according to claim 1, wherein the second electrode is made of a conductive material formed as a coating.

11. The device according to claim 1, wherein the second electrode covers over at least 30% of the height of the housing.

12. The device according to claim 1, wherein the second electrode covers over at least 40% of the height of the housing.

13. The device according to claim 1, wherein the cylinder shape is a circular cylinder shape.

14. The device according to claim 1, further comprising an acoustic sensor being coupled to the external wall of the arm band and having a sensitive side oriented away from the internal wall of the arm band, such that in use configuration, the sensitive side is adjacent to the chest of the user, to sense sound waves emitted by the heart.

15. The device according to claim 14, wherein the acoustic sensor is fixedly attached to the external wall of the arm band.

16. The device according to claim 14, wherein the acoustic sensor is removably attached to the external wall of the arm band.

17. The device according to claim 14, wherein the housing and the acoustic sensor are arranged at an angle $\alpha$ comprised between 90° and 140° with regard to a cylindrical configuration of a first portion, as defined in a use configuration on a 30 cm reference arm circumference.

* * * * *